(12) United States Patent
Attalla

(10) Patent No.: US 12,186,532 B2
(45) Date of Patent: Jan. 7, 2025

(54) APPARATUS AND METHOD FOR INJECTING MATERIAL INTO ORGANIC TISSUE

(71) Applicant: M. ATTALLA PTY LTD., Melbourne (AU)

(72) Inventor: Mark Attalla, Melbourne (AU)

(73) Assignee: M. ATTALLA PTY LTD, Melbourne (AU)

( * ) Notice: Subject to any disclaimer, the term of this patent is extended or adjusted under 35 U.S.C. 154(b) by 643 days.

(21) Appl. No.: 16/963,927

(22) PCT Filed: Jan. 24, 2019

(86) PCT No.: PCT/AU2019/050047
§ 371 (c)(1),
(2) Date: Jul. 22, 2020

(87) PCT Pub. No.: WO2019/144187
PCT Pub. Date: Aug. 1, 2019

(65) Prior Publication Data
US 2021/0038808 A1 Feb. 11, 2021

(30) Foreign Application Priority Data

Jan. 24, 2018 (AU) ................ 2018900221

(51) Int. Cl.
*A61M 5/168* (2006.01)
*A61K 35/28* (2015.01)
(Continued)

(52) U.S. Cl.
CPC ......... *A61M 5/16804* (2013.01); *A61K 35/28* (2013.01); *A61K 35/35* (2013.01);
(Continued)

(58) Field of Classification Search
CPC ...... A61M 5/00; A61M 5/46; A61M 5/16804; A61M 5/3158; A61M 5/31565;
(Continued)

(56) References Cited

U.S. PATENT DOCUMENTS 2,832,339 A 4/1958 Sarnoff et al.
2,888,924 A * 6/1959 Dunmire ............... A61M 5/282
604/199

(Continued)

FOREIGN PATENT DOCUMENTS

GB 190905440 A * 3/1909
GB 190905440 9/1909
(Continued)

OTHER PUBLICATIONS

Supplementary European Search Report issued in European Patent Application No. 19 74 3655 dated Sep. 24, 2021, 2 pages.
(Continued)

*Primary Examiner* — Emily L Schmidt
*Assistant Examiner* — Antarius S Daniel
(74) *Attorney, Agent, or Firm* — NIXON & VANDERHYE

(57) ABSTRACT

A problem with injecting cells such as fat cells into organic tissue to act as a filler material is that the cells must be distributed evenly and reasonably thinly to ensure that all of the injected cells are situated near to a blood supply and do not die. Injecting devices have been produced that use electronic controls and electro-mechanical mechanisms to improve distribution. The present approach however solves the problem of even distribution by coupling a skin surface sensing means to a plunger in a reservoir of the filler cells. In this way, the flow of cells out of a cannula relates directly to the rate at which the tip of the cannula penetrates the organic tissue into which the cells are being injected.

18 Claims, 5 Drawing Sheets

Figure 4:
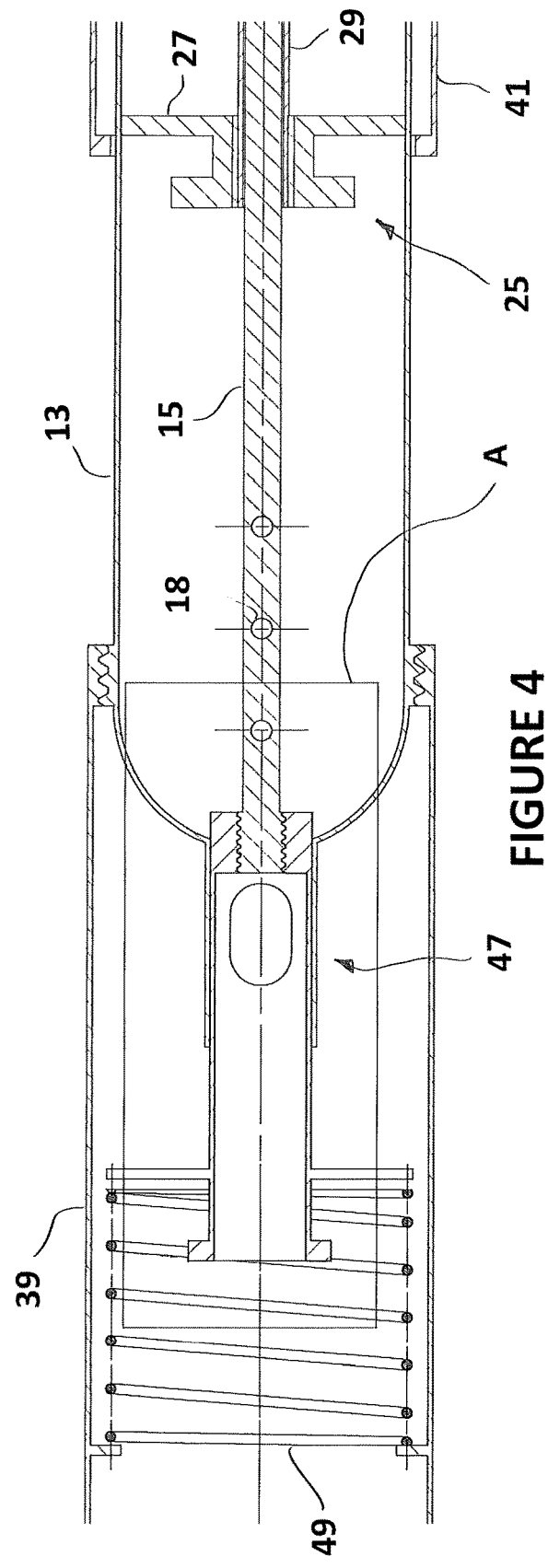

(51) Int. Cl.
*A61K 35/35* (2015.01)
*A61M 5/32* (2006.01)

(52) U.S. Cl.
CPC ....... *A61M 5/3291* (2013.01); *A61M 2202/08* (2013.01); *A61M 2205/13* (2013.01); *A61M 2205/3334* (2013.01)

(58) Field of Classification Search
CPC .......... A61M 2202/08; A61M 2205/13; A61M 25/0074; A61M 25/0075; A61M 39/26; A61M 2039/268; A61M 5/32; A61M 5/3291; A61K 35/35
See application file for complete search history.

(56) References Cited

U.S. PATENT DOCUMENTS

| | | | |
|---|---|---|---|
| 3,094,987 A * | 6/1963 | Dunmire | A61M 5/282 |
| | | | D24/115 |
| 7,569,035 B1 | 8/2009 | Wilmot et al. | |
| 2003/0168366 A1 * | 9/2003 | Hirsiger | A61M 5/326 |
| | | | 220/8 |
| 2014/0088553 A1 | 3/2014 | Hetherington | |
| 2014/0276452 A1 * | 9/2014 | Cowan | A61M 5/162 |
| | | | 604/244 |
| 2020/0276395 A1 * | 9/2020 | Zyman | A61M 5/42 |

FOREIGN PATENT DOCUMENTS

| | | | |
|---|---|---|---|
| WO | 2012/139593 | 10/2012 | |
| WO | WO-2012139593 A2 * | 10/2012 | ............ A61M 5/142 |

OTHER PUBLICATIONS

International-Type Search Report and Written Opinion for Australian Patent Application No. 2018900221 dated Apr. 23, 2018, 9 pages.
International Search Report for PCT/AU2019/050047 dated Mar. 1, 2019, 5 pages.
Written Opinion of the ISA for PCT/AU2019/050047 dated Mar. 1, 2019, 4 pages.

* cited by examiner

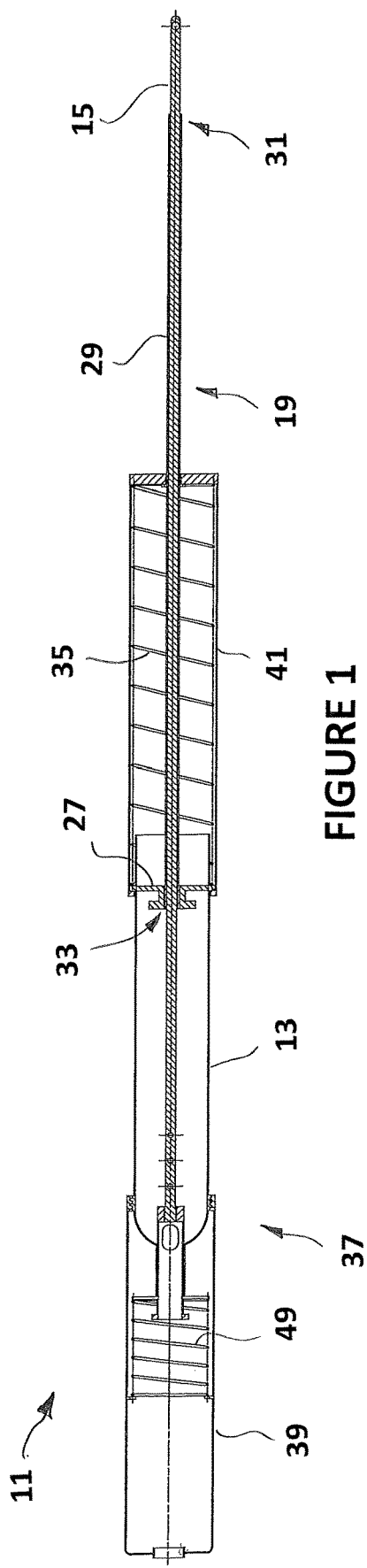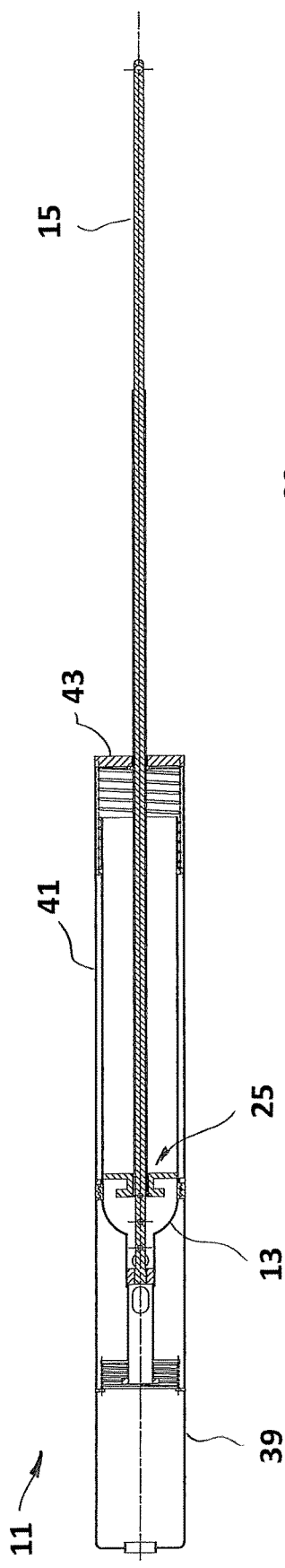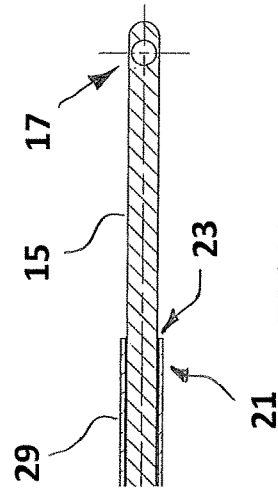

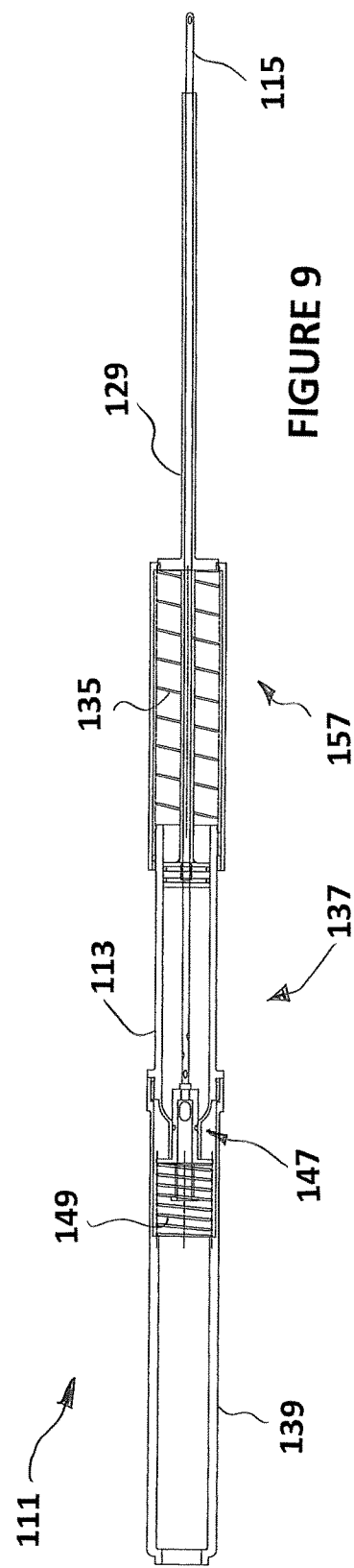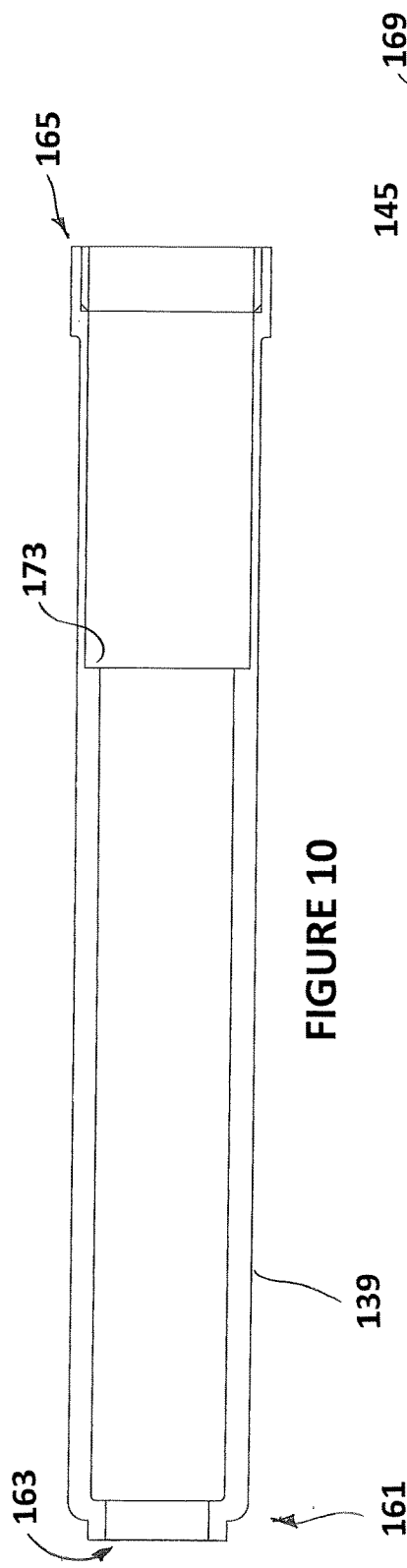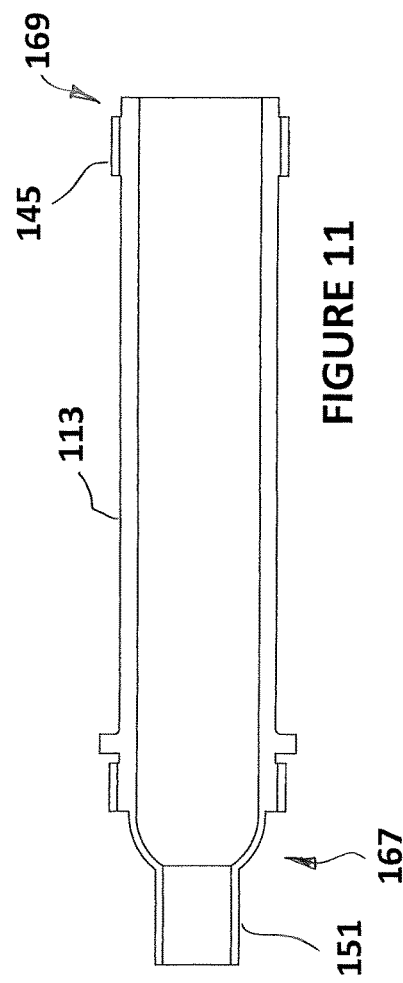

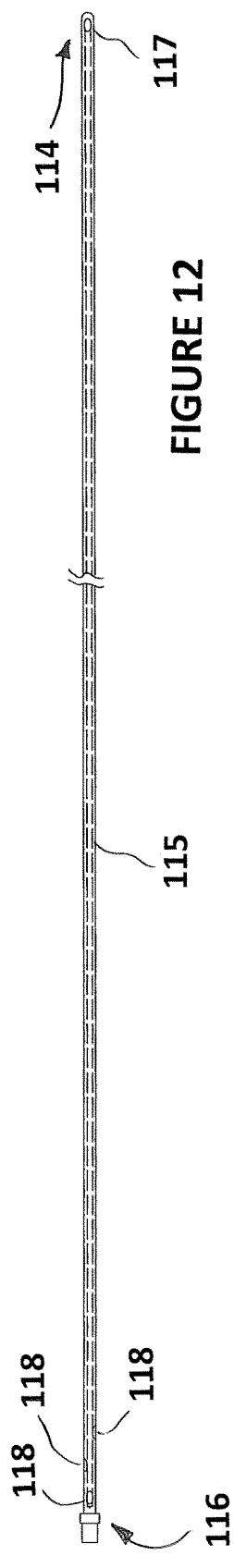
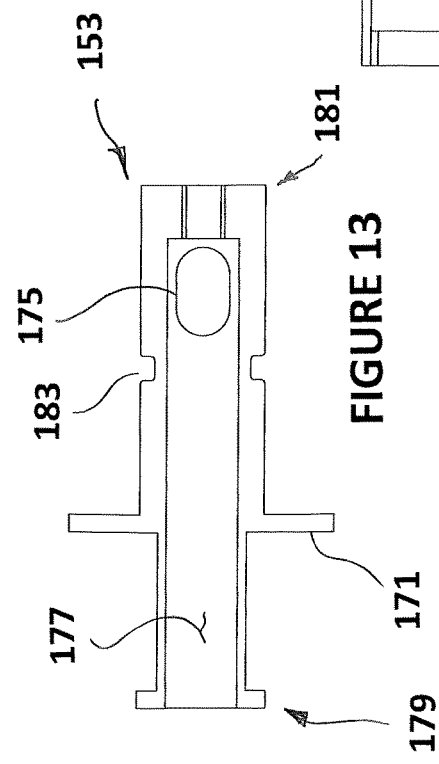
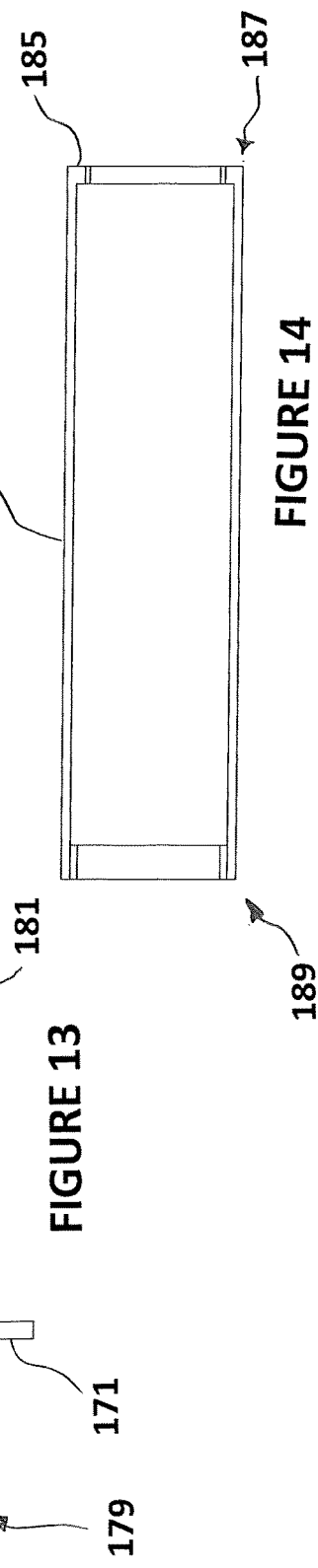
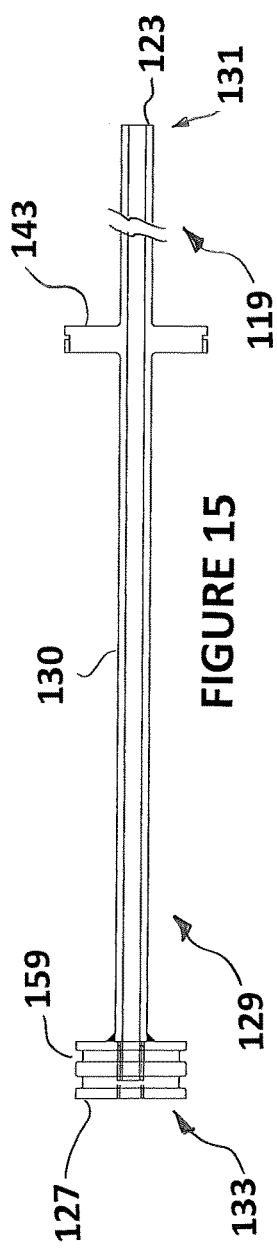

APPARATUS AND METHOD FOR INJECTING MATERIAL INTO ORGANIC TISSUE

This application is the U.S. national phase of International Application No. PCT/AU2019/050047 filed Jan. 24, 2019 which designated the U.S. and claims priority to AU patent application No. 2018900221 filed Jan. 24, 2018, the entire contents of each of which are hereby incorporated by reference.

FIELD OF THE INVENTION

This invention relates to an apparatus and method for injecting material into organic tissue, and in particular, but not exclusively to an apparatus and method for injecting fat cells or dermal fillers through the skin and into the subcutaneous tissue of humans.

BACKGROUND

The technique of taking or harvesting fat cells from one part of a person's body, that is, from a donor area, and then injecting the cells into another area to act as a filler or to reduce wrinkles, has been around for some time. The most common areas that fillers are injected are faces, breasts, legs and buttocks, and this procedure is often carried out for cosmetic reasons.

When living cells such as fat cells or stem cells are injected into human tissue it is important that only small quantities are injected adjacent to each blood vessel within the tissue, to ensure that the cells are each able to be sustained by the blood supply to the existing tissue. If too many cells are injected into one localised area or volume, many of those calls may die since they are not positioned close enough to a blood supply.

Early methods of depositing living cells into existing human tissue usually involved the manual injection of small quantities of cells into multiple sites. These methods relied heavily on operator skill, and in practice the procedures were not highly successful with the results being highly unpredictable, and the process of transferring living cells became unpopular especially for cosmetic purposes.

In more recent times, a range of devices have been developed that include trigger operated metering systems, geared systems, and even motor driven systems, with each being designed to reduce the influence of operator skill and to improve the reliability of the injection process by accurately metering the volume of cells being injected in any locality.

These improved devices have allowed improved success with the process of fat cell transfers and the procedure has gained favour again as a result.

The cell transfer process involves the accurate dispensing of small numbers of living cells into a large number of sites in the area being treated. Experience has shown that the operation of the newer devices, whether they be trigger operated, or by manual operation of a gear wheel, can be very tiring to operate and are a little cumbersome. In addition they require an assistant to help to regularly refill the devices to minimise the length of time to complete the procedure.

Electrically operated devices overcome the fatigue issue to some extent but can be a little complex and cumbersome to use and to maintain.

What is needed is a simpler system that can be used with relative ease, and which minimises operator error, and which distributes the living cells into the living tissue as evenly as possible.

In this specification unless the contrary is expressly stated, where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

OBJECT

It is therefore an object of the present invention to provide an apparatus and method for injecting material into organic tissue which will at least go some way towards overcoming one or more of the above mentioned problems, or at least provide the public with a useful choice.

STATEMENTS OF THE INVENTION

Accordingly, in a first aspect, the invention may broadly be said to consist in an apparatus for injecting material into organic tissue through a layer of skin, the apparatus having;
   a reservoir for holding a quantity of the material,
   a cannula with at least one outlet adjacent to a free end of the cannula and through which the material from the reservoir is injected into the organic tissue, and
   a skin surface sensing means;
and the apparatus is configured to distribute the material into the organic tissue between;
   a first depth in the organic tissue from the surface of the skin, and
   a second depth in the organic tissue from the surface of the skin;
and the skin surface sensing means controls the rate at which material is expelled from the cannula and into the organic tissue as the free end of the cannula is moved from the first depth and to the second depth.

Preferably the apparatus is configured such that the rate at which material is expelled through the or each outlet is proportional to the rate at which the free end of the cannula is moved through the organic tissue.

Preferably the skin surface sensing means includes a sensing member having a sensing face configured contact the surface of the skin covering the organic tissue.

Preferably the sensing face of the sensing member contacts the surface of the skin covering the organic tissue after the free end of the cannula is inserted through the surface of the skin, and when the outlet of the cannula reaches the said first depth.

Preferably the sensing face of the sensing member remains butted against the surface of the skin while the cannula is pushed further into the organic tissue.

Preferably the sensing member is mechanically linked to a plunger system of the injection apparatus.

Preferably the skin surface sensing means is coupled to a plunger of the plunger system, and the plunger is configured to push material out of the reservoir and through the or each outlet.

Preferably the skin surface sensing means includes an elongate member having a first end which includes the sensing member and a second end that is connected to the plunger.

Preferably the elongate member of the skin surface sensing means is in the form of a tubular sleeve situated about the cannula.

Preferably the apparatus includes a first biasing means that is configured to move the skin surface sensing means towards an extended position relative to a body of the apparatus.

Preferably the body includes a cylinder which forms the reservoir of the apparatus.

Preferably, when in use, movement of the body toward the organic tissue, and/or initial penetration of the free end of the cannula through a hole in the skin and into the organic tissue, causes the cannula to retract a predetermined amount relative to the body and to close a valve between the reservoir and a material supply line.

Preferably, when in use, continued movement of the body toward the organic tissue pushes a free end of the skin surface sensing means toward the skin surface about a hole in the skin surface through which the cannula has penetrated.

Preferably further movement of the body of the apparatus toward the organic tissue, after contact is made between the skin surface and the skin surface sensing means, causes the plunger to push material out of the reservoir and through the or each outlet hole.

Preferably the rate at which material is pushed out through the or each outlet hole is linked to the rate at which the cannula is pushed into the organic tissue.

Preferably the apparatus is connectable to a bulk supply of material via a flexible supply tube.

Preferably material flows from the bulk supply and into the reservoir when the valve is open and the skin surface sensing means is moving away from the body of the apparatus.

Preferably the apparatus includes a second biasing means that is configured to move the cannula toward an extended position relative to the body.

Preferably the first biasing means is in the form of a spring situated within a cylindrical housing that is connected to the skin surface sensing means.

Preferably the apparatus further includes a handle that is connected to the body or which is a part of the body.

In a second aspect, the invention may broadly be said to consist in a method of injecting material into organic tissue using an injection apparatus, including the steps of;

inserting a cannula of the injecting apparatus through a hole in the skin covering the organic tissue, and pushing the cannula into the organic tissue while a skin surface sensing means of the injection apparatus senses the depth of penetration of the cannula from the surface of the skin and into the organic tissue.

Preferably the skin surface sensing means controls the rate at which material is expelled from the reservoir and into the organic tissue via the cannula.

Preferably the skin surface sensing means includes a sensing member having a sensing face configured contact the skin covering the organic tissue.

Preferably the sensing face of the sensing member remains butted against the skin surface while the cannula is pushed into the organic tissue.

Preferably the sensing member is mechanically linked to a plunger system of the injection apparatus.

Preferably the rate at which material is expelled from the cannula is proportional to the rate at which the cannula is moved into the organic tissue.

The invention may also broadly be said to consist in the parts, elements and features referred to or indicated in the specification of the application, individually or collectively, and any or all combinations of any two or more of the parts, elements or features, and where specific integers are mentioned herein which have known equivalents, such equivalents are incorporated herein as if they were individually set forth.

DESCRIPTION

Figure 6:
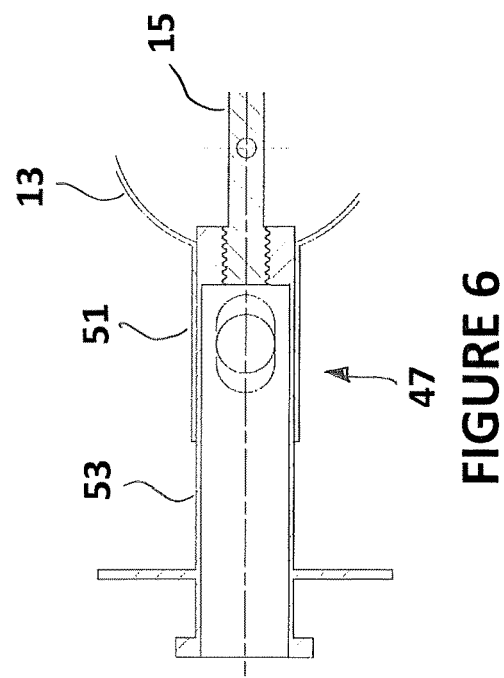
Figure 5:
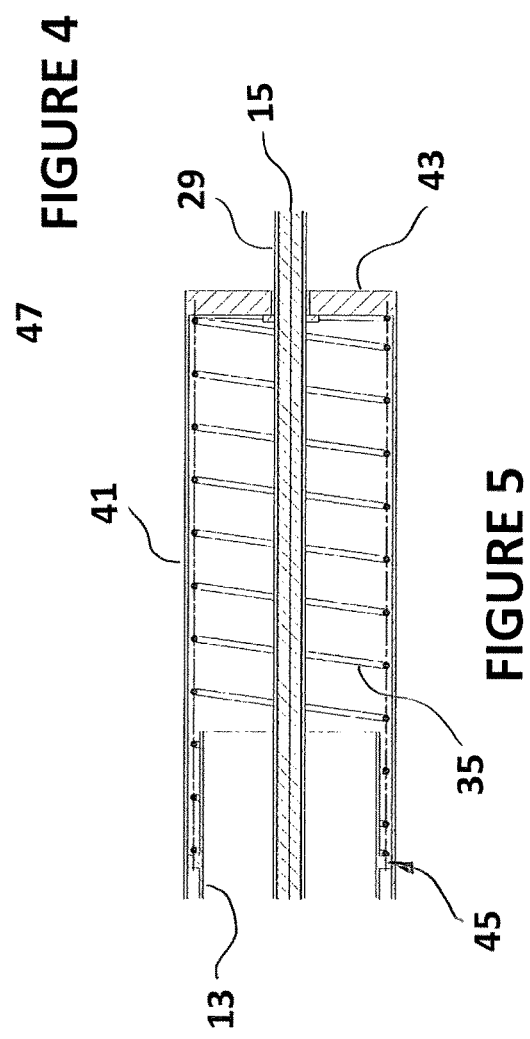
Figure 7:
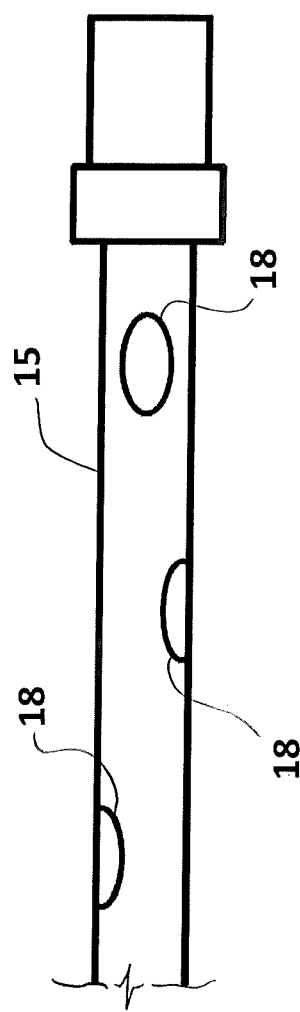
Figure 8:
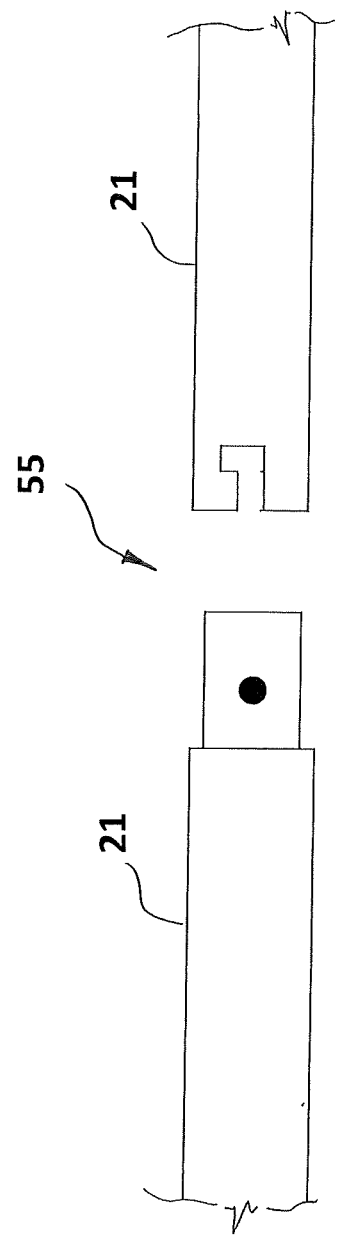

Further aspects of the present invention will become apparent from the following description which is given by way of example only and with reference to the accompanying drawings in which:

FIG. 1 is a longitudinal cross sectional view of a first example of an apparatus for injecting material into organic tissue according to the present invention, FIG. 2 is a longitudinal cross sectional view of the apparatus (first example) in a compressed state, FIG. 3 is an enlarged cross sectional view showing the end of a cannula of the apparatus (first example), FIG. 4 is an enlarged cross sectional view showing a reservoir section of the apparatus (first example) and defining a detail area "A", FIG. 5 is an enlarged cross sectional view showing a main return spring of the apparatus (first example), FIG. 6 is an enlarged cross sectional view of the detail area "A" defined in FIG. 4 showing a refill valve of the apparatus, FIG. 7 is an enlarged view of an inlet end of an alternative cannula design, FIG. 8 is an enlarged view of an optional join in the cannula, FIG. 9 is a longitudinal cross sectional view of a second example of an apparatus for injecting material into organic tissue according to the present invention, FIG. 10 is a cross sectional view of a handle of the apparatus (second example), FIG. 11 is a cross sectional view of a reservoir of the apparatus (second example), FIG. 12 is a side elevation view of a cannula of the apparatus (second example), FIG. 13 is a cross sectional view of a movable valve member of the apparatus (second example), FIG. 14 is a cross sectional view of a cylindrical housing of the apparatus (second example), and FIG. 15 is a partial cross sectional view of an elongate member of the apparatus (second example).

FIRST EXAMPLE

With reference to FIGS. 1 to 8, a first example of an apparatus (11) for injecting material into organic tissue according to the present invention will now be described. The apparatus (11) was designed for use in injecting material such as fat cells, fluids such as tumescent (used as a local anaesthetic in liposuction), dermal filler or stem cells into organic tissue. The apparatus (11) is typically used in cosmetic surgery to insert filler material into areas such as the face, legs, buttocks and breasts.

The apparatus (11) has a reservoir (13) for holding a quantity of filler material, and a cannula (15) through which the material from the reservoir (13) is injected into organic tissue. In this example, the cannula (15) has one outlet (17) that is situated adjacent to a free end of the cannula (15). With reference to FIG. 4 it can be seen that a fixed end of the cannula (15) is situated within the reservoir (13) and includes three inlet holes (18) through which the material can enter the cannula (15).

Importantly, the apparatus (11) also includes a skin surface sensing means (19) which will be described in further detail below.

The apparatus (11) is configured to distribute the material into the organic tissue between a first depth in the organic tissue from the surface of the skin and a second depth in the organic tissue from the surface of the skin. The skin surface sensing means (19) is used to control the rate at which material is expelled from the cannula (15) and into the organic tissue as the free end of the cannula (15) is moved from the first depth and to the second depth. The rate at which material is expelled through the outlet (17) is proportional to the rate at which the free end of the cannula (17) is moved through the organic tissue.

The skin surface sensing means (19) includes a sensing member (21) having a sensing face (23) configured contact the surface of the skin covering the organic tissue. The sensing face (23) of the sensing member (21) contacts the surface of the skin covering the organic tissue after the free end of the cannula (15) is inserted through a hole in the surface of the skin. The hole in the surface of the skin is generally produced by first pricking the skin with a sharp needle. The sensing face (23) of the sensing member (21) remains butted against the surface of the skin while the cannula (15) is pushed further into the organic tissue.

In this example, the sensing member (21) is mechanically linked to a plunger system (25) associated with the reservoir (13) of the injection apparatus (11). The skin surface sensing means (19) is coupled to a plunger (27) of the plunger system (25) and the plunger (27) is situated within the reservoir (13) and is configured to push material out of the reservoir (13) and along the length of the cannula (15) and through the outlet (17) into the organic tissue.

The skin surface sensing means (19) includes an elongate member (29) having a first end (31) which includes the sensing member (21) and a second end (33) that is connected to the plunger (27). The elongate member (29) is in the form of a tubular sleeve that is situated about the cannula (15) and which slides longitudinally relative to the cannula (15).

The apparatus (11) further includes a first biasing means in the form of a first coil spring (35) that is configured to move the skin surface sensing means (19) towards an extended position relative to a body (37) of the apparatus (11). The body (37) includes a barrel or cylinder which forms the reservoir (13) of the apparatus (11). The apparatus (11) further includes a handle (39) that is rigidly connected to the cylinder that forms the reservoir (13).

The first coil spring (35) is situated within a cylindrical housing (41). The cylindrical housing (41) is open at one end and includes a bulkhead (43) at an opposite end. The open end of the cylindrical housing (41) fits over the cylinder or barrel that forms the reservoir (13), while leaving space for the first coil spring (35) to fit and move between the outside diameter of the cylinder that forms the reservoir (13) and the inside diameter of the cylindrical housing (41). The first coil spring (35) is a compression spring that is compressed between a circumferential ridge (45) about the reservoir (13) and the bulkhead (43) of the cylindrical housing (41).

The cylindrical housing (41) is connected to the skin surface sensing means (19) via a threaded joint between the bulkhead (43) and the elongate member (29). When the tubular sleeve of the elongate member (29) slides into the body (37) along the cannula (15) the first coil spring (35) is compressed.

The apparatus (11) is connectable to a bulk supply of material via a flexible material supply tube (not shown). When in use, movement of the body (37) toward the organic tissue, and/or initial penetration of the free end of the cannula (15) through a hole in the skin and into the organic tissue, causes the cannula (15) to retract a predetermined amount relative to the body (37) and thereby to close a valve (47) situated between the reservoir (13) and the material supply tube.

The valve (47) is situated within the handle (39) and the apparatus further includes a second biasing means in the form of a second coiled compression spring (49) that is configured to move the cannula (15) a short distance toward an extended position relative to the body (37). The valve (47) includes a valve body (51) that is attached to the reservoir (13), and also includes a movable valve member (53). The movable valve member (53) is connected to the cannula (15) via a threaded joint, and the movable valve member (53) is moved by movement of the cannula (15). Movement of the movable valve member (53) relative to the valve body (51) either opens or closes a flow passage through the valve (47). The compression spring (49) is compressed when the cannula (15) initially retracts, and moves the movable valve member (53) away from the reservoir (13), and the valve (47) is being closed.

Continued movement of the body (37) toward the organic tissue pushes a free end of the skin surface sensing means (19) toward the skin surface about the hole in the skin through which the cannula (15) has penetrated, until the sensing face (23) butts against the skin surface about the hole.

Further movement of the body (37) toward the organic tissue after contact is made between the skin surface and the sensing face (23) causes the elongate member (29) to retract within, or move toward, the body (37). Retraction of the elongate member (29) within the body (37), or towards the body (37), causes the plunger (27) to move within the reservoir (13) and to push material out of the reservoir (13) and into the cannula (15) through the inlet holes (18), and down the length of the cannula and through the outlet hole (17) and into the organic tissue. In this way, the rate at which material is pushed out through the outlet hole (17) and into the organic tissue is linked to the rate at which the cannula (15) is being pushed into the organic tissue, thereby producing an even spread of the material within the organic tissue between the first depth and the second depth.

After the reservoir (13) has been partially or completely depleted, as shown in FIG. 2, the reservoir (13) is replenished when material is drawn from the bulk supply and flows into the reservoir (13). This happens after the second biasing member (49) pushes the cannula (15) a short distance out of the body (37), thereby moving the movable valve member (53) toward the reservoir (13) and opening the valve (47). The material is drawn into the reservoir (13) through the valve (47), as the skin surface sensing means (19) is moved away from the body (37) by the first coil spring (35), which in turn drags the plunger (27) along the reservoir (13) to create a suction to help draw the material into the reservoir (13).

With reference to FIG. 7, an alternative inlet end of the cannula (15) is shown. In this alternative embodiment, the inlet holes (18) which allow material to enter into an internal bore of the cannula (15) are slightly larger than in than those shown in FIG. 4. The reason for the increase in size is to allow material such as fat cells to flow into the cannula (15) with less resistance and therefore less stress on the cells. The freer flow of material into the cannula (15) also reduces strain on the operator. In this example the inlet holes (18) are each elliptically shaped, with a major axis of the elliptical shape being two millimetres long and a minor axis of the elliptical shape being one millimetre long.

In each case, the inlet holes (18) pass all the way through the cannula (15). Also in this alternative embodiment, the three inlet holes (18) are not aligned with each other, but rather each successive hole is indexed about the circumference of the cannula (15) with respect to the other inlet holes. And in this example, a principal axis of each inlet hole (18), in a direction through the cannula (15), and when viewed from either end of the cannula (15), is aligned at sixty degrees to a principal axis of the other two inlet holes (18).

The sensing member (21) (or the elongate member (29)) can be made up of two or more lengths that are joined end to end, and FIG. 8 shows an optional bayonet style joint (55) that can be used to join adjacent lengths of the sensing member (21). This construction method allows a longer cannula (15) to be used if required, to allow material to be injected to a greater depth in the organic tissue.

SECOND EXAMPLE

With reference to FIGS. 9 to 15, a second example of an apparatus (111) for injecting material into organic tissue according to the present invention will now be described. The apparatus (111) is a development of the first example (11) described above, and incorporates a number of features to improve the performance, primarily by improving flow and preventing leakage from the reservoir.

As with the first example of an apparatus (11), the apparatus (111) has a reservoir (113) for holding a quantity of material, and a cannula (115) through which the material from the reservoir (113) is injected into organic tissue. The cannula (115) is approximately 280 to 300 millimetres long and has an outlet (117) that is situated adjacent to a free end (114) of the cannula (115). A fixed end (116) of the cannula (115) is situated within the reservoir (113) and material is pushed into the cannula (115) from the reservoir through three inlet holes (118) that are situated adjacent the fixed end (116) of the cannula (115).

Each of the inlet holes (118) pass all the way through the cannula (115) and they intersect and communicate with an internal longitudinal passageway of the cannula (115). Each inlet hole (118) is elliptical in shape, a principal axis of each elliptical shape being aligned with a principal axis of the cannula. The cannula (115) has a diameter of approximately 1.8 millimetres, and a longitudinal bore or passageway having a diameter of approximately 0.8 millimetres, and each elliptical shaped inlet hole (118) is approximately two millimetres long and one millimetre wide.

As with the configuration described with reference to FIG. 7, the three inlet holes (118) of the cannula (115) of this second example of an apparatus (111) are not aligned with each other, but rather are aligned in spiralled arrangement. Due to the spiral arrangement, each successive hole (118) is indexed about a circumference of the cannula (115) with respect to the other inlet holes. And in this example, a principal axis of each inlet hole (118), in a direction through the cannula (115), and when viewed from either end of the cannula (115), is aligned at sixty degrees to a principal axis of the other two inlet holes (118).

The fixed end (116) of the cannula (115) includes an externally threaded ferrule that mates with an internal thread on an outlet end (155) of a movable valve member (153) of a refill valve (147). In this way, the cannula (115) is mechanically fastened to the movable valve member (153) and can be used to move the movable valve member (153) to close the refill valve (147), to allow the reservoir (113) to be pressurised by the movement of the plunger (127).

A middle section of the cannula (115) is situated within an elongate guide member (129). The elongate guide member (129) includes an elongate tube (130) which acts as a tubular sleeve and as a guide for the cannula (115) to move within. The elongate tube (130) has an internal diameter of approximately two millimetres that slides over and moves along the middle section of the cannula (115). The elongate guide member (129) also includes skin sensing face (123) at a first or free end (131), and a plunger (127) at a second or enclosed end (133).

The plunger (127) is mated to the elongate tube (130) using a threaded connection, and the joint also includes a fillet weld to help seal the joint and to prevent inadvertent loosening of the joint. The plunger (127) also includes external seal grooves (159) about its circumference that allow seals such as O-rings to be used to create a leak resistant joint between the plunger (127) and an internal diameter of the reservoir (113).

The elongate guide member (129) also has a bulkhead section (143) that is a part of the elongate tube (130) and is situated approximately midway between the first end (131) and the second end (133), but closer to the second end (133) than the first end (131). In this example, the elongate guide member (129) is approximately two hundred and ten millimetres long and the bulkhead section (143) is situated approximately eighty millimetres from the second end (133).

The bulkhead section (143) of the elongate tube (130) is circular in shape and includes an external thread about its circumference. The external thread of the bulkhead section (143) mates with an internal thread on a fixed end (187) of a cylindrical housing (141). In this way, the elongate guide member (129) is mechanically fastened to the cylindrical housing (141), and movement of the elongate guide member (129) produces a similar movement of the cylindrical housing (141).

The cylindrical housing (141) comprises a tube that is approximately eighty millimetres long and has an inside diameter of approximately twenty millimetres, and has a threaded section at each end. The cylindrical housing (141) is configured to fit over the reservoir (113) and to slide along its length.

With reference to FIG. 9 it can be seen that the apparatus (111) comprises two main assemblies that can move in a longitudinal sliding motion relative to each other. A first main part, or body (137), comprises the reservoir (113) and a handle (139). And the second main part, or slide (157), comprises the cylindrical housing (141) and the elongate member (129). The slide (157) slides relative to the body (137) when the apparatus (111) is in use. A third main part of the apparatus (111) is the cannula (115) which is connected to the body (137) via a movable connection provided by the refill valve (147). The cannula (115) is supported along a part of its length by the slide (157), while at the same time being able to move longitudinally relative to the slide (157).

Both the reservoir (113) and the handle (139) are essentially cylindrically shaped housings. The handle (139) is approximately one hundred and thirty millimetres long and has an outside diameter of approximately eighteen millimetres. The length of one hundred and thirty millimetres is helpful in making the handle (139) easy to grasp and to control movement of the apparatus (111) when in use. A free end (161) of the handle (139) includes an opening (163) through which a refill tube can be inserted to provide a supply of material to the reservoir (113) via the refill valve (147). A fixed end (165) of the handle (139) includes an internal thread that is configured to mate with an external thread on a fixed end (167) of the reservoir (113). In this way the handle (139) is mechanically fastened to the reservoir (113) to form the body (137) of the apparatus (111).

The slide section (157) is initially mated to the body section (137) by inserting the plunger (127) of the slide section (157) into a free end (169) of the reservoir (113) of the body section (137). As the slide section (157) is further mated to the body section (137), the cylindrical housing (141) begins to telescope over the outside diameter of the reservoir (113). The mating process further involves rotating the cylindrical housing (141) relative to the reservoir (113) to allow an internal thread on a free end (189) of the cylindrical housing (141) to engage with, and to move over, an externally threaded circumferential band or ridge (145) that is situated adjacent the free end (169) of the reservoir (113).

When fully assembled, the internal thread on the free end of the cylindrical housing (141) has passed fully over the externally threaded band (145) of the reservoir (113), and the cylindrical housing (141) can move or be telescoped over a greater part of the length of the reservoir (113). When fully assembled, movement of the slide section (157) relative to the body section (137), and towards the handle (139), causes the plunger (127) to move up the cylinder (113) with the result that material within the cylinder (113) is pressurised and is caused to flow through the inlet holes (118) and into the cannula (115).

A first coil spring (135) is a compression spring which is situated within the cylindrical housing (141), with a first end butted against a lip (185) on the fixed end of the cylindrical housing (141), and with a second end of the spring (135) butted against the free end (169) of the reservoir (113). In this way, the first spring (135) biases the slide section (157) in a direction away from the handle (139) of the body section (137). In use, the slide section (157) can be pushed onto the body section (137) until the first spring (135) is fully compressed. When the first spring (135) is fully extended the plunger (127) is situated adjacent the free end (169) of the reservoir (113), and when the first spring (135) is fully compressed the plunger (127) is situated adjacent the fixed end (167) of the reservoir (113).

The apparatus (111) is relatively easy to use compared to prior art injecting devices because it includes a skin surface sensing means (119) that controls the rate at which material is injected into organic tissue. The skin surface sensing means (119) comprises a skin surface sensing member (121) which is essentially the first, or free end (131) of the elongate tube (130). The free end (131) of the elongate tube (130) includes a sensing face (123).

When the apparatus (111) is in use, the free end (114) of the cannula (115) is inserted through a small incision that is made in the skin of a client who is receiving filler material. As the cannula (115) is inserted further into the tissue of the client, the sensing face (123) of the skin surface sensing means (119) will contact the skin. Continued movement of the apparatus (111) toward the tissue will cause the cannula (115) to progressively pass deeper into the tissue while the slide section (157) of the apparatus (111) is held back due to the contact between the sensing face (123) and the skin surface of the client.

This causes the slide section (157) to move relative to the body section (137), compressing the first spring (135). When this happens, the plunger (127) is progressively moved up the reservoir (113) causing material to be dispensed out of the cannula (115) and into the tissue. In this way, the amount of material that is dispensed out of the cannula (115) is relative to the distance moved by the cannula (115) into the tissue. The distance that the cannula (115) moves into the tissue relates directly to the distance that the plunger (127) is caused to move within the reservoir (113), and the distance that the plunger (127) moves relates directly to the volume of material that is pushed out of the reservoir (113) and into the tissue.

The reservoir (113) of the injecting apparatus (111) is refilled via the refill valve (147). The refill valve (147) is operated by pushing the cannula (115) toward the handle (139) against the force of a second compression spring (149). One end of the second spring (149) butts against a flange (171) of the movable valve member (153), and an opposite end of the second spring (149) butts against a shoulder (173) formed in the inside diameter of the handle (139).

The movable valve member (153) includes an internal passage (177) which is an internal passageway which runs along the length of the valve member (153) from a connection end (179) that is configured to mate with a refill line, to an outlet end (181) where a valve outlet aperture (175) is situated.

The second spring (149) biases the movable valve member (153) toward a 'valve open' position in which the valve outlet aperture (175) is situated within the chamber of the reservoir (113) and is not covered by a cylindrically shaped valve body (151). In this position it is possible to refill the reservoir (113) by pushing material into the reservoir through the refill valve (147), or by drawing or sucking material into the reservoir (113) by pulling the slide section (159) away from the handle (139), or by allowing the first spring (135) to push the slide section (159) away from the handle (139), or by a combination of these methods.

The cylindrically shaped valve body (151) is essentially a length of tubing, approximately ten millimetres long and nine millimetres in diameter, that is formed as an extension of the reservoir (113), being situated at, and extending from, the fixed end of the reservoir (113). The axis of the valve body (151) is aligned with the axis of the reservoir (113). The movable valve member (153) has an O-ring groove (183) situated about its outer diameter for a seal or O-ring to minimise leakage between the outside diameter of the valve member (153) and the inside diameter of the valve body (151).

During use of the apparatus (111), when the cannula (115) is being inserted into organic tissue, the cannula (115) is initially moved back toward the handle (139) causing the movable valve member (153) to move in the same direction. This initial backward movement of the cannula (115) compresses the second spring (149) and closes the refill valve (147) by positioning the valve outlet aperture (175) within the valve body (151) where the valve outlet aperture (175) is closed off by the valve body (151).

With the refill valve (147) closed the plunger (127) is then able to pressurise the inside of the reservoir to dispense material out through the outlet (117) as the free end (114) of the cannula (115) moves deeper into the tissue, and the slide section (157) is pushed toward the handle (139). As noted above, material is dispensed out through the outlet (117) in a controlled manner, with the rate at which material is dispensed being proportional to the rate at which the outlet (117) is moved from a starting or first depth to a second or final depth within the organic tissue in which the filler material is being deposited.

Method of Operation

The method of injecting material into organic tissue using the first example of an apparatus (11) can be summarised as follows;

- the reservoir (13) is initially filled from a bulk supply of suitable material through the valve (47) (this is the configuration shown in FIG. 1),
- the cannula (15) is inserted through a hole in the skin covering the organic tissue and the cannula is initially retracted a small amount into the body (37) and closes the valve (47),
- the cannula (15) is pushed a short distance through the skin until the skin surface sensing means (19) determines that the cannula (15) has reached the first depth,
- the free end of the cannula (15) is pushed into the organic tissue from the first depth to the second depth further while the skin surface sensing means (19) senses the depth of penetration of the cannula (15) from the surface of the skin and into the organic tissue,
- the skin surface sensing means (19) controls the rate at which material is expelled from the reservoir and into the organic tissue via the cannula as the cannula (15) is pushed into the organic tissue from the first depth to the second depth,
- upon initial withdrawal of the cannula (15) from the organic tissue the cannula extends a small amount from the body (37) under the force exerted by the second biasing means and thereby opens the valve (47), and
- continued withdrawal of the cannula (15) from the organic tissue allows the elongate member of the skin surface sensing means (19) to extend under the influence of the first biasing means, causing the plunger (27) to draw fresh material into the reservoir from the bulk supply, making the apparatus (11) ready for the next injection process.

The method of operation of the second example of an apparatus (111) is essentially the same as the method of operation of the first example of an apparatus (11) described herein. In the description section above, the parts of the second example have similar item numbers (with a "1" in front) to their equivalent parts in the first example, that is a part with item number (53) in the first example is numbered (153) in the second example. The similarly numbered items can be used in the method outlined herein to define the method of operation of the apparatus (111) of the second example.

Variations

Aspects of the present invention have been described by way of example only and it should be appreciated that modifications and additions may be made thereto without departing from the scope thereof.

In the example described herein, the skin surface sensing, or the amount of penetration of the cannula into the tissue, is carried out mechanically. However, in an alternative embodiment it is envisaged that skin surface sensing, or the amount of penetration of the cannula into the tissue could be determined by other means, for example optical sensing, ultra sound sensing or other imaging techniques and the rate at which material is expelled from the cannula could be controlled electronically using a microprocessor and an electrically driven actuator to drive the plunger.

The cannula in the examples described includes a single outlet. It is envisaged that the cannula could be provided with additional outlets, for example an outlet on the opposite side of the cannula, if desired.

The apparatus (11 or 111) is envisaged primarily for use in injecting fat cells, stem cells or dermal fillers into humans, however it is envisaged that the apparatus could be used to inject material into the tissue of animals or a range of other living organisms including plant life if desired.

As an alternative to a single outlet hole (17 or 117) in the cannula (15 or 115), the cannula can have multiple outlet holes, for example three outlet holes arranged in a spiralled alignment.

Definitions

Throughout this specification the word "comprise" and variations of that word, such as "comprises" and "comprising", are not intended to exclude other additives, components, integers or steps.

Advantages

Thus it can be seen that at least the preferred form of the invention provides an apparatus and/or method for injecting material into organic tissue which is simple and low cost, and easy to operate, and which can distribute material evenly within the organic tissue without requiring great technical skill to operate. From this point of view, the operation of the apparatus (11) or (111) could be considered semiautomatic in that the operator simply has to insert the cannula at any desired rate and the apparatus automatically adjusts the rate at which material is injected to match the rate of insertion of the cannula.

In addition the apparatus as shown and described does not include any complex mechanical or electrical devices or circuitry and for this reason is lower cost, simpler to operate and maintain, and also simpler and more hygienic to clean.

The invention claimed is:

1. An apparatus for injecting material into organic tissue through a layer of skin, the apparatus comprising;
    a reservoir for holding a quantity of the material,
    a cannula with at least one outlet adjacent to a free end of the cannula and through which the material from the reservoir is injected into the organic tissue,
    a plunger situated within the reservoir, and
    a skin surface sensing means situated about the cannula and mechanically coupled to the plunger;
and the apparatus is configured to distribute the material into the organic tissue between;
    a first depth in the organic tissue from the surface of the skin, and
    a second depth in the organic tissue from the surface of the skin;
wherein a first end of the skin surface sensing means is configured to contact the surface of the skin after the free end of the cannula is inserted through the surface of the skin and reaches the first depth, and a second end of the skin surface sensing means is configured to retract within the reservoir and cause the plunger to move the free end of the cannula from the first depth to the second depth and push the material out of the reservoir and through the at least one outlet of the cannula;
wherein the apparatus comprises a valve which is configured to refill the reservoir of the apparatus from a material supply connected to the apparatus when the apparatus is in use.

2. The apparatus for injecting material into organic tissue as claimed in claim 1, wherein the skin surface sensing means comprises a tubular sleeve including a sensing face at the first end which is configured to contact the surface of the skin.

3. The apparatus for injecting material into organic tissue as claimed in claim 2, wherein the sensing face of the sensing member remains in contact with the surface of the skin while the cannula is pushed further into the organic tissue by the plunger.

4. The apparatus for injecting material into organic tissue as claimed in claim 1, wherein the second end of the skin surface sensing means is coupled to the plunger, and the plunger is configured to push material out of the reservoir and into the cannula through at least one inlet, and out of the cannula into the organic tissue through the at least one outlet.

5. The apparatus for injecting material into organic tissue as claimed in claim 4, wherein a fixed end of the cannula is situated within the reservoir and comprises a plurality of inlet holes through which the material can enter the cannula.

6. The apparatus for injecting material into organic tissue as claimed in claim 5, wherein the inlet holes are elliptically shaped and situated about the circumference of the cannula in a non-aligned manner or in a spiralled arrangement.

7. The apparatus for injecting material into organic tissue as claimed in claim 1, wherein the apparatus includes a first biasing means that is configured to move the skin surface sensing means towards an extended position relative to a body of the apparatus.

8. The apparatus for injecting material into organic tissue as claimed in claim 1, wherein a body of the apparatus includes a cylinder which forms the reservoir of the apparatus.

9. The apparatus for injecting material into organic tissue as claimed in claim 1, wherein a rate at which material is pushed out through the at least one outlet is linked to a rate at which the cannula is pushed into the organic tissue.

10. A method of injecting material into organic tissue using an injection apparatus, including the steps of;
  inserting the cannula of the injecting apparatus of claim 1 through a hole in the skin covering the organic tissue, and
  pushing the cannula into the organic tissue while the skin surface sensing means of the injection apparatus senses the depth of penetration of the cannula from the surface of the skin and into the organic tissue.

11. The method of injecting material into organic tissue as claimed in claim 10, wherein the skin surface sensing means controls a rate at which material is expelled from the reservoir and into the organic tissue via the cannula.

12. The method of injecting material into organic tissue as claimed in claim 11, wherein the rate at which material is expelled from the cannula is proportional to a rate at which the cannula is moved into the organic tissue.

13. The method of injecting material into organic tissue as claimed in claim 10, wherein the skin surface sensing means includes a sensing member having a sensing face configured to contact the skin covering the organic tissue.

14. The method of injecting material into organic tissue as claimed in claim 13, wherein the sensing face of the sensing member remains butted against the skin surface while the cannula is pushed into the organic tissue.

15. The apparatus for injecting material into organic tissue as claimed in claim 1, wherein the valve includes a moveable valve member operatively connected to the cannula, and movement of the cannula causes a flow passage through the valve to open or close.

16. An apparatus for injecting material into organic tissue through a layer of skin, the apparatus having;
  a reservoir for holding a quantity of the material,
  a cannula with at least one outlet adjacent to a free end of the cannula and through which the material from the reservoir is injected into the organic tissue, and
  a skin surface sensing means;
and the apparatus is configured to distribute the material into the organic tissue between;
  a first depth in the organic tissue from the surface of the skin, and
  a second depth in the organic tissue from the surface of the skin;
and the skin surface sensing means controls a rate at which material is expelled from the cannula and into the organic tissue as the free end of the cannula is moved from the first depth and to the second depth;
  wherein, when in use, movement of a body of the apparatus toward the organic tissue, and/or initial penetration of the free end of the cannula through a hole in the skin and into the organic tissue, causes the cannula to retract a predetermined amount relative to the body and to close a valve between the reservoir and a material supply line.

17. The apparatus for injecting material into organic tissue as claimed in claim 16, wherein, when in use, continued movement of the body toward the organic tissue pushes a free end of the skin surface sensing means toward the skin surface about a hole in the skin surface through which the cannula has penetrated.

18. The apparatus for injecting material into organic tissue as claimed in claim 17, wherein further movement of the body of the apparatus toward the organic tissue, after contact is made between the skin surface and the skin surface sensing means, causes the plunger to push material out of the reservoir and through the at least one outlet.

* * * * *